(12) United States Patent
Fan et al.

(10) Patent No.: US 11,808,745 B2
(45) Date of Patent: Nov. 7, 2023

(54) GAS SAMPLING WITH CONTROLLED HUMIDITY

(71) Applicant: Calyx, Inc., Berkeley, CA (US)

(72) Inventors: Benson Fan, Berkeley, CA (US); Po-Jui Chiu, Berkeley, CA (US); Chun Yi Leu, Taipei (TW); I-Ting Chen, Taipei (TW); Ming-Yuan Tsai, New Taipei (TW)

(73) Assignee: Calyx, Inc., Berkeley, CA (US)

( * ) Notice: Subject to any disclaimer, the term of this patent is extended or adjusted under 35 U.S.C. 154(b) by 0 days.

(21) Appl. No.: 17/266,907

(22) PCT Filed: Oct. 7, 2019

(86) PCT No.: PCT/US2019/055043
§ 371 (c)(1),
(2) Date: Feb. 8, 2021

(87) PCT Pub. No.: WO2020/047558
PCT Pub. Date: Mar. 5, 2020

(65) Prior Publication Data
US 2021/0341444 A1    Nov. 4, 2021

Related U.S. Application Data

(60) Provisional application No. 62/716,822, filed on Aug. 9, 2018.

(51) Int. Cl.
*G01N 33/00* (2006.01)
*G01N 1/22* (2006.01)

(52) U.S. Cl.
CPC ....... *G01N 33/0016* (2013.01); *G01N 1/2205* (2013.01); *G01N 2001/2282* (2013.01)

(58) Field of Classification Search
CPC ............ G01N 33/0016; G01N 1/2205; G01N 2001/2282
See application file for complete search history.

(56) References Cited

U.S. PATENT DOCUMENTS

| | | | |
|---|---|---|---|
| 5,368,786 A | 11/1994 | Dinauer et al. | |
| 7,493,795 B2 | 2/2009 | Komura et al. | |
| 7,753,991 B2* | 7/2010 | Kertzman | A61M 16/1075 128/205.27 |
| 2002/0170559 A1* | 11/2002 | Nitta | A61M 16/109 128/203.12 |
| 2005/0081715 A1 | 4/2005 | Goodwin et al. | |

(Continued)

FOREIGN PATENT DOCUMENTS

| | | | | |
|---|---|---|---|---|
| DE | 0789239 A1 | * | 4/1997 | ............. G01N 33/00 |
| EP | 0789239 A1 | * | 8/1997 | ............. G01N 33/00 |
| WO | WO-2017138024 A2 | * | 8/2017 | ........... G01N 1/2205 |

*Primary Examiner* — David Z Huang
(74) *Attorney, Agent, or Firm* — David T. Millers

(57) ABSTRACT

A sensor system (100) or a sensing method minimizes the loss of aroma chemicals or other analytes in a sample gas while controlling the temperature and humidity of the sample gas. The system (100) may employ a humidifier (120) that adds water vapor to sample gas to provide a known water content, e.g., a saturated humidity at a known temperature. A sensing unit (130) may accurately measure the composition of the sample gas having a known water content, e.g., at a higher known temperature.

17 Claims, 1 Drawing Sheet

(56) References Cited

U.S. PATENT DOCUMENTS

| | | | |
|---|---|---|---|
| 2005/0119607 A1* | 6/2005 | Van Der Linden | A61B 90/40 |
| | | | 604/23 |
| 2015/0108670 A1* | 4/2015 | Magee | A61M 16/1095 |
| | | | 261/142 |
| 2017/0184531 A1* | 6/2017 | Snelders | G01N 27/221 |
| 2018/0172655 A1* | 6/2018 | Motayed | G01N 33/0031 |
| 2018/0250490 A1* | 9/2018 | Burgess | A61M 16/147 |

* cited by examiner

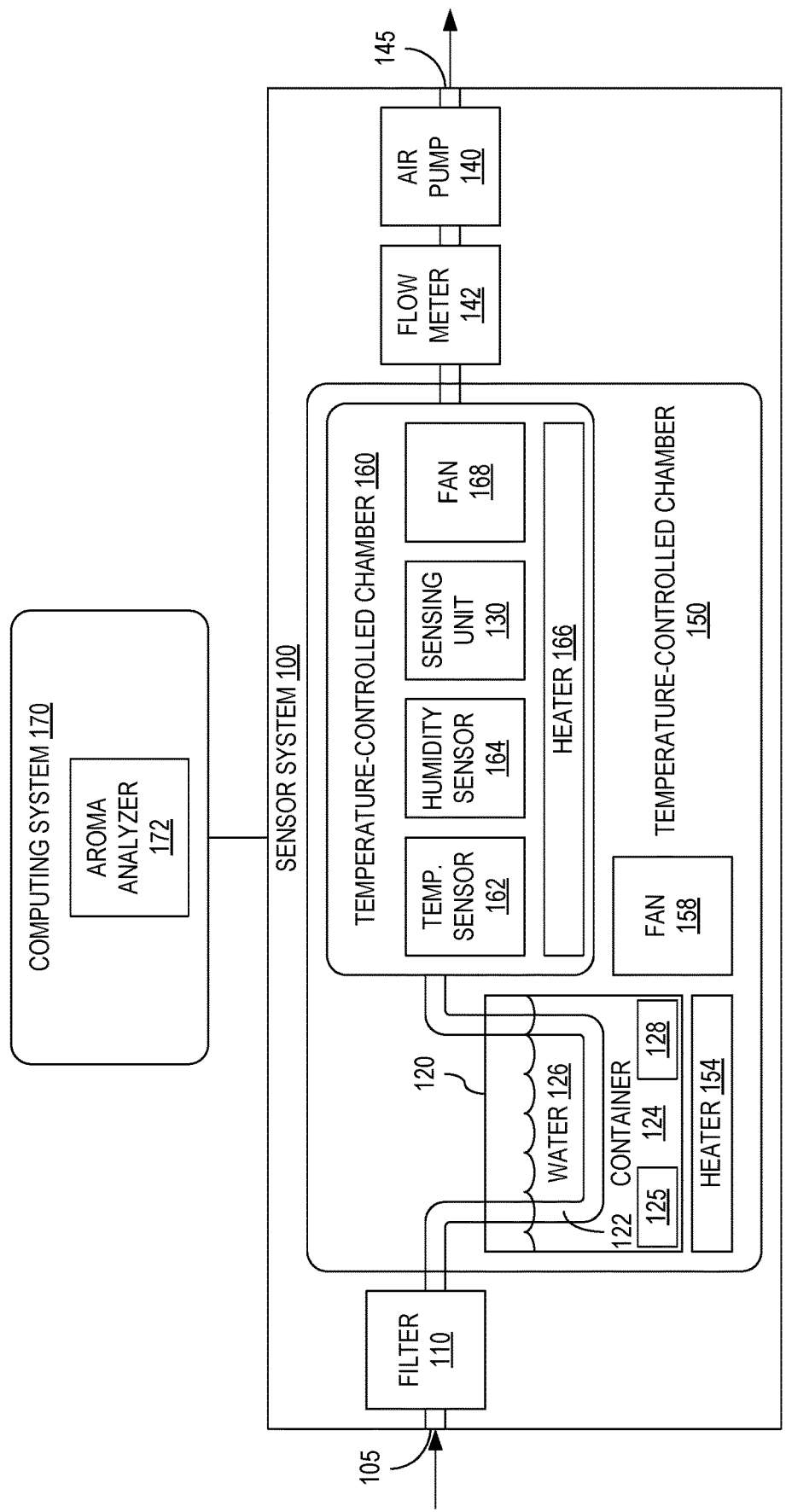

GAS SAMPLING WITH CONTROLLED HUMIDITY

CROSS-REFERENCE TO RELATED APPLICATIONS

This patent document is a U.S. national stage of PCT App. No. PCT/US2019/055043, filed Oct. 7, 2019, which claims benefit of the earlier filing date of U.S. Provisional Pat. App. No. 62/716,822, filed Aug. 9, 2018, which is hereby incorporated by reference in its entirety.

BACKGROUND

Atmospheric or gas sensors and analyzers have used many different mechanisms to measure the composition of sample gas or to sense the presence or quantity of particular compounds in a sample gas. For example, gas sensors may be based on detecting or measuring electrochemical, mechanical, catalytic, or conductive changes that result from the presence or a particular concentration of one or more target chemical in a sample gas. One challenge for environmental sensors is avoiding undesirable effects that changing environmental parameters may cause when sensors try to precisely measure small amounts of target chemicals. Environment parameters such as temperature, humidity, and pressure, may be constantly changing, which, if not properly addressed, may change the response a sensor has to the target chemical, resulting in inaccurate measurement data.

One way to compensate for the effects of changing humidity and temperature is through data normalization. Data normalization measures the humidity and temperature when measurements are taken and adjusts raw sensor readings based on the measured humidity and temperature to produce adjusted sensor readings. Although this technique may work for simple gas sensing, in situations where multiple gases or analytes are targeted, data-based normalization or adjustments may be difficult to perform. Aroma sensing may, for example, need to sense relative or absolute concentrations of hundreds of different compounds in a sample.

An alternative approach may attempt to remove variable quantities such as humidity from a gas sample, to create a water-free sample. Removing humidity, however, generally requires use of chemicals desiccants that bind or otherwise interact strongly with water. The use of desiccating chemicals may, however, have variable effects on other constituents of the sample and thereby alter the composition of the gas sample so that the sample is not indicative of the original environment. Accordingly, new sensors and new sampling methods are needed to control variable environmental conditions in gas samples and particularly to preserve the composition of a sample gas for aroma sensing.

BRIEF DESCRIPTION OF THE DRAWING

FIG. 1 is a block diagram of one implementation of a sensor system that controls the humidity of a gas sample, particularly for the example of aroma sensing.

The drawing illustrates an example for the purpose of explanation and is not of the invention itself.

DETAILED DESCRIPTION

In accordance with an aspect of the present invention a sensor or a sensing process can minimize the loss of aroma chemicals or other analytes or otherwise minimize changes in the composition in a sample gas, while controlling the temperature and humidity of the sample gas for accurate measurement or detection.

The drawing shows one implementation of a gas sensor system 100 that allows collection of gas samples with controlled temperature and humidity for accurate sensing. Sensor system 100 may, for example, be an aroma sensor designed to measure the presence or concentration of many, typically hundreds of, distinct chemicals or analytes in the sample gas. In one configuration, sensor system 100 has at least two openings, an inlet 105 for receiving gas and an outlet 145 for gas exhaust. The opening sizes can vary depending on the purpose or the specific application of sensor system 100. Sensor system 100 further includes a filter 110, a humidifier 120, a sensing unit 130, and an air or gas pump 140. In typical application, gas pump 140 draws sample gas, e.g., air containing chemicals causing aromas, from a surrounding environment through inlet 105, filter 110, and humidifier 120 to sensing unit 130 and exhausts gas from sensor system 100 through outlet 145.

Filter 110 receives gas, e.g., air from the surrounding environment, at gas inlet 105 and may include one or more gas-permeable filter membranes, as well as a mesh, covering inlet 105. Filter 110 may be a particulate filter configured to remove particles such as dust and water droplets or steam from sample gas entering sensor system 100. For example, filter 110 may include one or more layers of porous filter membrane. The filter material can be of various pore sizes and may be made of water proof materials such as Teflon. Filter 110 may further include filter media or stuffing between the membranes, and the between-membrane filter media may include beads of various sizes made of hydrophobic and/or hydrophilic materials. Air from the open environment thus enters filter 110, where dust particles and water droplets are filtered out.

Clean sample gas from filter 110 flows through humidifier 120, which may be inside a temperature-controlled chamber 150. In the illustrated configuration humidifier 120 includes a tube 122 that directs a flow of sample gas from filter 110 through humidifier 120 to another temperature-controlled chamber 160. Humidifier 120 is inside temperature-controlled chamber 150 and, in the illustrated configuration, includes a container or reservoir 124 containing water 126, which may specifically be liquid water in container 124. Container 124 may, for example, be a small tank or reservoir capable of holding between 50 milliliters and one liter of water. Container 124 may have a stirring apparatus 125 in water 126 for mixing to provide water 126 with a uniform temperature, and a temperature probe or sensor 128 may be used to measure the temperature of water 126. A heater 154 and a fan 158 in temperature-controlled chamber 150 may be operated to maintain a desired, constant, uniform temperature for air or other gas in chamber 150 and/or to maintain a desired, constant, uniform temperature for water 126 in container 124 and any other contents of chamber 150. Alternatively, heater 154 may be in container 124 or primarily used to heat water 126 in container 124. In either case, water vapor from container 124 may saturate the humidity of air or other gas in chamber 150 or alternatively just saturate the humidity of air or gas passing through tube 122 to chamber 160. Tube 122 may be gas permeable or may have a gas permeable portion to permit entry of water vapor into the clean sample gas flowing through tube 122. For example, tube 122 may include a gas-permeable membrane that loops into and is submerged under liquid water 126 in container 124 upstream from where tube 122 comes back out of container 124 and connects to chamber 160. Tube 122 or the gas permeable portion of tube 122 can be of various lengths and sizes depending on the gas flow through sensor system 100 and may be made of Nafion®, Teflon®, polyamide, cellulose acetate, or a suitable ceramic material. As a result of the gas permeability of tube 122, a water vapor pressure in the sample gas may be set to a target level, e.g., the sample gas may have a saturated humidity at the temperature maintained in chamber 150.

In one specific implementation, heater 154 is an electrical element or heating rod that operates, e.g., turns on and off, to keep the temperature of chamber 150 and/or water 126 at a level such that sample air passing through humidifier 120 achieves a target temperature and humidity, e.g., sample air leaving humidifier 120 may have 100% relative humidity at the temperature of chamber 150. In one specific implementation, the temperature of the gas in chamber 150 and water 126 in reservoir 124 may be elevated above the temperature of the surrounding environment, e.g., kept between about 15 and 40° C. or specifically at about 20° C. in a room temperature surrounding environment.

Humidified sample air from humidifier 120 enters temperature-controlled chamber 160, which contains sensing unit 130. In the illustrated configuration, chamber 160 may include or contain a temperature sensor 162, a humidity sensor 164, a heater 166, and a fan 168, in addition to sensing unit 130. Temperature sensor 162 senses the temperature of sample gas in chamber 160 and may control heater 166 to establish or maintain a desired temperature for the sample gas in chamber 160, and fan 168 may be used to circulate the sample gas in chamber 160 to maintain a uniform temperature of the sample gas throughout chamber 160. For example, heater 166 may be an electrical element or heating rod, and temperature sensor 162 may be a thermostat connected and configured to activate heater 166 if the temperature of the sample gas falls below a desired lower limit and turn off heater 166 if the temperature of the sample air rises above a desired upper limit. In particular, sample gas in sensing chamber may be kept at a nearly-constant temperature, which may be chosen based on the desired or target water vapor content of the sample gas in chamber 160. In one specific implementation, the temperature of sample gas in sensing chamber 160 may be the higher than the temperature of chamber 150, e.g., between about 15 and 45° C. or at about 25° C., to lower the humidity of the sample gas at sensing unit 130 to a known and controlled target level. Humidity sensor 164 may be employed to ensure that the desired humidity is being achieved.

Sensing unit 130 may employ any desired sensing technology or sensing techniques suitable for detecting target chemicals or gases in the sample gas. Sensing unit 130 may, for example, include one or more different sensors for the measurement of different analytes, gases, chemicals, or aromas. In one specific embodiment, sensing unit 130 includes an array of photoconductive nanostructure/nanocluster hybrid sensors enabling light-assisted sensing of target analytes such as described in U.S. Pat. App. Pub. No. 2018/0172655, entitled "Method for Manufacturing an Array of Sensors on a Single Chip," which is hereby incorporated by reference in its entirety. In accordance with an aspect of the present invention, sensing unit 130 can provide particularly precise and consistent measurements of the composition of the sample gas or of specific target chemicals in the sample gas because the temperature and humidity of the sample gas in chamber 160 is known and controlled to be at target levels.

Measurements or sensing data from sensing unit 130 may be directed through a wired or wireless connection or network to a computing system 170, which may include an aroma analyzer 172. Computing system 170 may be a conventional computing system such as a smart phone, a tablet computer, lap top computer, or a desk top computer executing a suitable application that implements aroma analyzer 172. Computing system 170 could alternatively include a microcontroller system or application hardware that implements aroma analyzer 172 in or for sensor system 100. Aroma analyzer 172 may, for example, be implemented in an application or firmware executed by computing system 170. Aroma analyzer 172 receives sensor data from sensor system 100 and performs multivariable analysis on the sensor data to determine which, if any, identifiable aroma is being sensed by sensor system 100. In particular, an identifiable aroma may correspond to specific combination of relative concentrations of many different target chemicals that sensing unit 130 can measure, and different identifiable aromas may be distinguished as corresponding to different combinations of the relative concentrations of the target chemicals.

Gas pump 140 operates to draw sample gas out of chamber 160 and exhaust the measured sample gas out of sensor system 100, e.g., back into the ambient or environment surrounding sensor system 100. The draw of gas from chamber 160 causes further flow of gas from the ambient into filter 110 and through humidifier 120 into chamber 160, so that sensor system 100 may continuously sample gas from the ambient environment and the sensing unit 130 in chamber 160 may continuously measure characteristics of the ambient gas in the environment surrounding sensor system 100. Gas pump 140 can draw the sample gas at various flow rate selected depending on the use or application of sensor system 100. The flow rate of pump 140 may be altered. For example, the flow rate may be adjusted based on the feedback from a flow meter 142.

Sensor system 100 may have several advantages over prior sensor systems. In particular, rather than removing humidity from the input gas samples using desiccants that may be a consumable and may chemically alter the sample gas, sensor system 100 during its operation adds humidity to the input sample, e.g., so that the humidity of the sample becomes saturated, for consistent and accurate measurements of sample composition. Sensor system 100 can also sample gas in real time and does not require storing sample gas or any use of stored gases. Sensor system 100 may also maintain a sensing chamber at a constant, elevated temperature, so that the humidity and temperature level coming in to the sensor unit 130 remain constant.

More specific examples of sensing process are described further below. With these processes, regardless of the sample input and condition, the sample gas has humidity and temperature that is controlled and consistent when the sample gas is introduced to sensing unit 130.

Sensor system 100, in one example, may be used to sense the aroma of coffee. For example, 200 ml of liquid coffee may be freshly prepared and hot, in a room environment of 20° C. and a room relative humidity of 50%. Sensor system 100 may activate gas pump 140 to draw in a gas sample when gas inlet 105 is near, e.g., placed right above, the liquid coffee. The inlet membrane and filter 110 removes water drops or condensation from the gas sample, as well as any dust particles that could otherwise pass further into sensor system 100. The gas sample that enters gas inlet 105 may be close to 100% relative humidity level if the inlet is close to steaming coffee but the sample gas from filter 110 does not include condensation or steam. The gas sample may be increased in temperature in chamber 150, while humidifier 120 adds additional humidity into the gas sample. The humidity level of sample gas from humidifier 120 may be saturated at the known temperature, e.g., 20° C., of chamber 150, and hence has steady humidity and water content. The gas sample then enters sensor chamber 160, which may be a higher controlled temperature, e.g., 25° C. The increase in temperature decreases relative humidity down to a constant level, e.g., about 74% humidity, before sensing unit 130 measures the sample gas. The sample gas is then exhausted from the outlet of sensor system 100, and the measurement data from sensing unit 130 can be provided to aroma analyzer 172. Aroma analyzer 172 can analyze the measurement data, which was obtained at the target temperature and humidity, to detect a coffee aroma.

Sensor system 100 in another example sensing process is placed adjacent to about 10 grams of coffee beans in a bowl, in a room environment of 18° C. and 60% relative humidity. Sensor system 100 activates gas pump 140 to draw in a gas sample using the gas inlet 105, that may be right above the coffee beans. The entrance membrane and filter 110 filters out any dust particles that might otherwise enter sensor system 100. The gas sample that enters the inlet 105 may have a temperature and humidity that is close to the temperature and humidity of the room environment, e.g., about 18° C. and 60% relative humidity. The temperature of the gas sample may be elevated, e.g., to 20° C., at humidifier 120. Humidifier 120 adds additional humidity (water vapor) into the gas sample, so the humidity level of the sample gas is then close to a 100% relative humidity level (saturated) at the temperature, e.g., 20° C., of chamber 150, and hence has steady humidity. The sample gas then enters sensor chamber 160, that is temperature controlled at 25° C. The humidity is then brought down to a constant level of about 74% relative humidity due to the temperature increase in chamber 160, and sensing unit 130 senses or measures the sample gas before the sample gas is exhausted from sensor system 100, and the measurement data from sensing unit 130 can be provided to aroma analyzer 172. Aroma analyzer 172 can analyze the measurement data, which was again obtained at the target temperature and humidity, to detect a coffee aroma.

All or portions of some of the above-described systems and methods can be implemented in a computer-readable media, e.g., a non-transient media, such as an optical or magnetic disk, a memory card, or other solid state storage containing instructions that a computing device can execute to perform specific processes that are described herein. Such media may further be or be contained in a server or other device connected to a network such as the Internet that provides for the downloading of data and executable instructions.

Although particular implementations have been disclosed, these implementations are only examples and should not be taken as limitations. Various adaptations and combinations of features of the implementations disclosed are within the scope of the following claims.

What is claimed is:
1. A gas sensor comprising:
a humidifier configured to add water vapor to a sample gas that contains one or more chemicals at respective levels to be measured;
a first temperature control system configured to heat the sample gas to a first temperature at which the humidifier adds water vapor to the sample gas;
a sensing unit coupled to receive the sample gas from the humidifier, the sensing unit measuring the levels of the one or more chemicals while the sample gas includes the water vapor that the humidifier added; and
a second temperature control system configured to heat the sample gas from the first temperature to a second temperature at which the sensing unit measures the levels of the one or more chemicals.

2. The gas sensor of claim 1, wherein the humidifier saturates humidity of the sample gas at the first temperature.

3. The gas sensor of claim 2, wherein the second temperature is higher than the first temperature.

4. The gas sensor of claim 1, wherein the humidifier comprises:
a container holding water; and
a tube including a gas permeable section through which the humidifier adds the water vapor to the sample gas.

5. The gas sensor of claim 4, wherein the tube passes through the water in the container.

6. The gas sensor of claim 4, wherein the first temperature control system comprises a first temperature-controlled chamber containing the humidifier and keeping the humidifier and the sample gas at the first temperature while the humidifier adds water vapor to the sample gas.

7. The gas sensor of claim 1, wherein the second temperature control system comprises:
a chamber containing the sensing unit and coupled to receive the sample gas including the water vapor that the humidifier added;
a heater positioned to heat the sample gas in the chamber; and
a temperature sensor coupled to control the heater and maintain the second temperature.

8. The gas sensor of claim 1, further comprising a filter system positioned to receive the sample gas input to the gas sensor, the filter system removing particulates and water droplets from the sample gas input to the gas sensor.

9. A process for sensing one or more chemicals, the process comprising:
obtaining a gas sample in which the one or more chemicals may be present at respective levels to be measured;
filtering particulates and water droplets from the gas sample;
heating the gas sample to maintain a first temperature of the gas sample at a humidifier;
adding water vapor to the gas sample to provide the gas sample with a target relative humidity at the first temperature;
heating the gas sample with the added water vapor from the first temperature to a second temperature; and
while the gas sample is at the second temperature, measuring the gas sample with the water vapor added, the measuring sensing the levels of the one or more chemicals in the gas sample.

10. The process of claim 9, wherein heating the sample gas to maintain the first temperature comprises heating the gas sample from an ambient temperature that the gas sample had when obtained to the first temperature.

11. The process of claim 9, wherein the one or more chemicals comprises a plurality of chemicals, and measuring the gas sample comprises:
exposing an array of photoreactive sensors, which respectively sense the plurality of chemicals, to the gas sample; and
determining the presence or the levels of the plurality of chemicals from responses of the photoreactive sensors to the gas sample.

12. The process of claim 11, further comprising identifying an aroma of the gas sample from the levels of the plurality of chemicals.

13. The gas sensor of claim 1, wherein the sensing unit comprises an array of photoreactive sensors.

14. The gas sensor of claim 1, wherein the sensing unit comprises a plurality of sensors that respectively sense a plurality of chemicals that create aromas.

15. An aroma sensor comprising:
- a humidifier connected to receive a gas sample that contains a plurality of aroma chemicals at respective levels to be measured to identify an aroma, the aroma chemicals being chemicals that when combined in different combinations present different aromas;
- a first temperature control system configured to heat the gas sample to maintain the gas sample at a first temperature while the humidifier adds water vapor to the gas sample and produces a humidified gas sample having a first humidity at the first temperature;
- a sensing unit connected to receive the humidified gas from the humidifier and to measure the levels of the aroma chemicals in the humidified gas sample, the levels measured indicating the aroma identified; and
- a second temperature control system configured to control a second temperature of the humidified gas sample such that the humidified gas sample has a second humidity while the sensing unit measures the levels of the aroma chemicals.

16. The aroma sensor of claim 15, wherein the sensing unit comprises an array containing photoreactive sensors that respectively sense the aroma chemicals.

17. The aroma sensor of claim 15, wherein the first humidity saturates the gas sample at the first temperature, and wherein the second humidity does not saturate the sample gas at the second temperature.

* * * * *